United States Patent [19]

Ghim

[11] 4,432,715
[45] Feb. 21, 1984

[54] MOLTEN MATERIAL DISPENSING APPARATUS

[76] Inventor: Duk K. Ghim, 11 Merlin St., Framingham, Mass. 01701

[21] Appl. No.: 353,492

[22] Filed: Mar. 1, 1982

[51] Int. Cl.³ .................... B29F 5/00; B29D 9/00
[52] U.S. Cl. .................... 425/87; 118/101; 222/146 HE; 251/251; 401/1; 425/458
[58] Field of Search ............ 118/200, 620, 101; 401/1, 2, 3, 21, 25, 26, 27, 136, 137, 139, 203, 204, 263, 265, 266, 268, 278, 282; 425/87, 447, 458, DIG. 13; 251/229, 251; 222/146 HE

[56] References Cited

U.S. PATENT DOCUMENTS

| | | | |
|---|---|---|---|
| 535,257 | 3/1895 | Moore | 401/263 |
| 704,577 | 7/1902 | Puff | 401/266 |
| 972,431 | 10/1910 | Beggs | 251/251 |
| 1,754,330 | 4/1930 | Litomy | 401/1 |
| 2,070,206 | 2/1937 | Hudson | 401/263 |
| 2,107,686 | 2/1938 | Bramsen et al. | 251/229 |
| 2,187,586 | 1/1940 | Hooper | 251/229 |
| 2,708,095 | 5/1955 | Mitchell | 251/229 |
| 3,332,108 | 7/1967 | Bustamante | 425/87 |
| 3,662,927 | 5/1972 | Cocks | 401/1 |
| 3,853,410 | 12/1974 | Busoni | 401/1 |
| 3,864,045 | 2/1975 | Hudson | 401/1 |
| 4,260,272 | 4/1981 | Lebecque | 401/266 |

FOREIGN PATENT DOCUMENTS

| | | | |
|---|---|---|---|
| 89612 | 2/1922 | Austria | 401/266 |
| 1684452 | 10/1969 | Fed. Rep. of Germany | 401/263 |
| 59307 | 3/1954 | France | 401/263 |

Primary Examiner—Willard E. Hoag
Attorney, Agent, or Firm—John E. Toupal; Harold G. Jarcho

[57] ABSTRACT

A molten substance dispenser including a container for a substance to be dispensed, a hand manipulatable applicator for applying liquified material received from the container to a work piece, a flexible tube for accommodating flow of the liquified material between the container and the applicator, and heater means for heating the liquified substance in the container, the applicator and the flexible tube.

7 Claims, 7 Drawing Figures

MOLTEN MATERIAL DISPENSING APPARATUS

BACKGROUND OF THE INVENTION

This invention relates generally to a molten material dispenser and, more particularly, to a dispenser that can provide a continuous flow of molten material and be manually employed to create models of a desired object.

In certain fields, molten wax is used to form models that are subsequently used to mold desired objects from less workable materials such as metal or plasic. Such techniques are extensively utilized, for example, in the creation of dental appliances and jewelry. Typically, a suitable mold material such as plaster is deposited around the wax models which are then melted to form a cavity that can be used to mold the final object. Technicians involved in such activities generally employ small spatulas that are first held over a suitable heat source such as gas or an electrically fired Bunsen burner and then positioned in solid wax, some of which melts. After being melted, the wax in the spatula is manually applied to create the desired wax model. Obviously, the requirement for repetitively melting a small quantity of wax in a hand held spatula before each application of melted wax to the desired model results in a procedure that is tedious, awkward and very time consuming. A further disadvantage is that liquid wax can be dispensed from the open spatulas only in a downward direction. In many instances, it would be desirable to apply liquid wax to the underside of a model during its design growth.

The object of this invention, therefore, is to provide an improved melted wax dispenser that can be manually utilized in the creation of pattern molds.

SUMMARY OF THE INVENTION

The invention is a molten substance dispenser including a container for a substance to be dispensed, a hand manipulatable applicator for applying liquified material received from the container to a work piece, a flexible tube for accommodating flow of the liquified material between the container and the applicator, and heater means for heating the liquified substance in the container, the applicator and the flexible tube. The application of heat to each of the container, applicator and supply tube components insures a continuous availability of molten material.

According to one feature of the invention, the heating means includes an electrically conductive heater wire extending through the flexible supply tube. The use of a heater wire disposed within the supply tube insures a continuously liquid state for the material therein and simplifies the structural requirements of the dispenser unit.

According to another feature of the invention, the heater wire includes additional section lengths disposed in heat exchanging relationship with both the container and the hand held applicator. A power supply associated with the container provides heating current flow through the heater wire.

According to another feature of the invention, the dispenser includes a valve member supported by the applicator and operable to control the flow of molten material through a discharge port therein. The valve can be used at a technician's discretion to provide intermittent flow of molten material during the creation of a model.

According to yet another feature of the invention, the valve member includes a bias spring for biasing the valve into a closed position and a valve operator easily manipulatable by a finger on a hand holding the applicator. The provision of a valve operator manipulatable by the same hand that is holding the applicator greatly facilitates the use of the device during the formation of a model.

In a featured embodiment of the above-featured invention, the valve operator includes a cam surface for forcibly engaging the valve member to produce movement thereof toward an open position. The cam surface permits a user to easily control the rate of molten material flow with a single finger on a hand manipulating the applicator.

Another feature of the invention is the provision of a plurality of interchangeable dispenser heads that can be selectively mounted on the applicator. The plurality of dispenser heads are uniquely suited for different applications and enhance the overall utility of the device.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENTS

Figure 1:
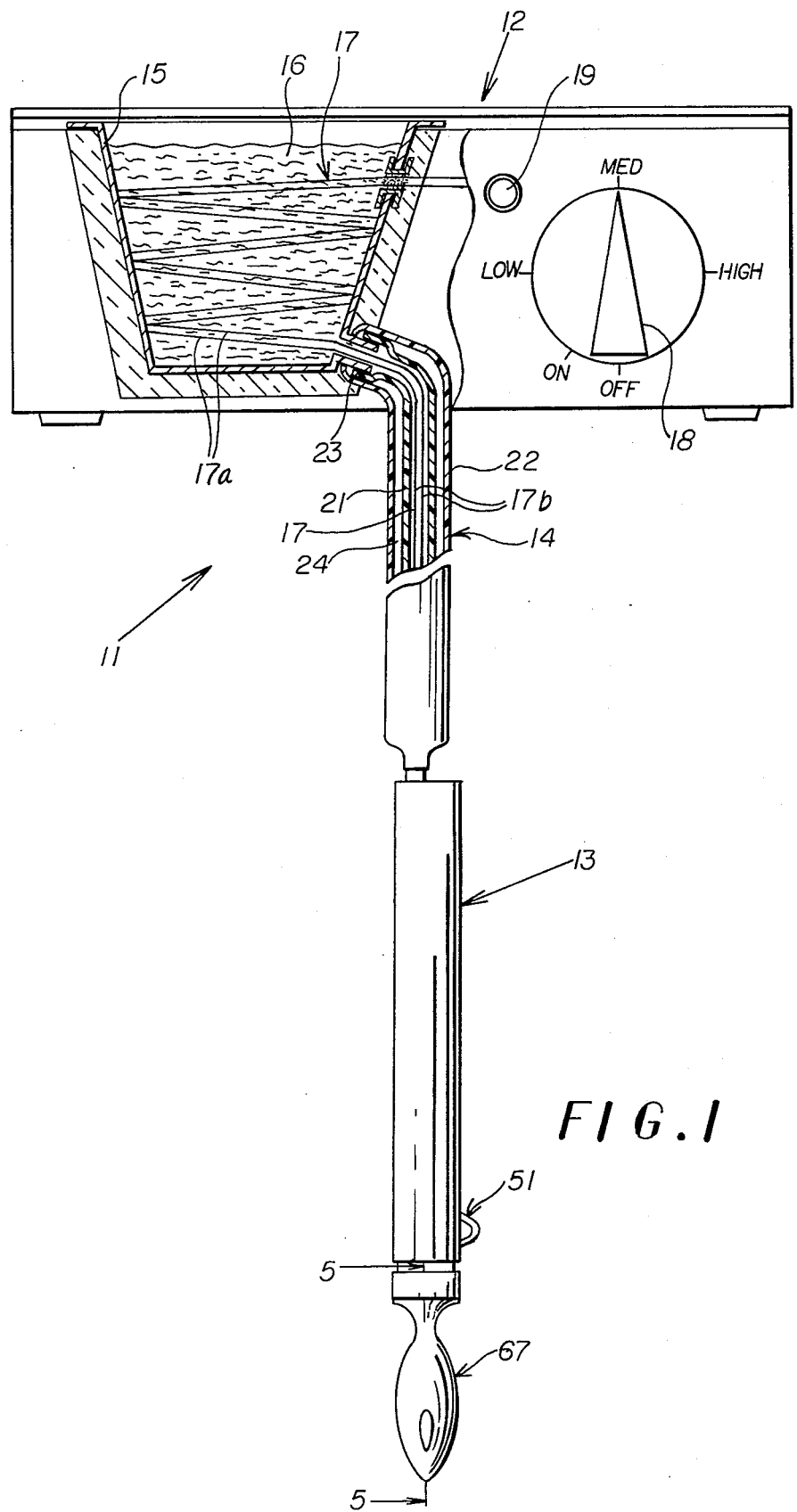
FIG. 1 is a schematic view, partly in cross section, showing a dispenser device according to the invention.

FIG. 1 is a schematic view of a dispenser device 11 for use in creating wax models. Included in the device 11 is a combined heat control and wax supply unit 12, a hand manipulatable applicator unit 13 and a flexible tube 14 connected therebetween. The unit 12 includes a container 15 filled with a suitable wax substance 16. Coiled along the inner surface of the container 15 is an electrical heater wire section 17a of a wire 17 that is connected to a power supply (not shown) within the unit 12. The flow of heating current between the power supply and the heater wire 17 is regulated by a control knob 18 and an indicator lamp 19 provides a visual indication thereof.

Figure 2:
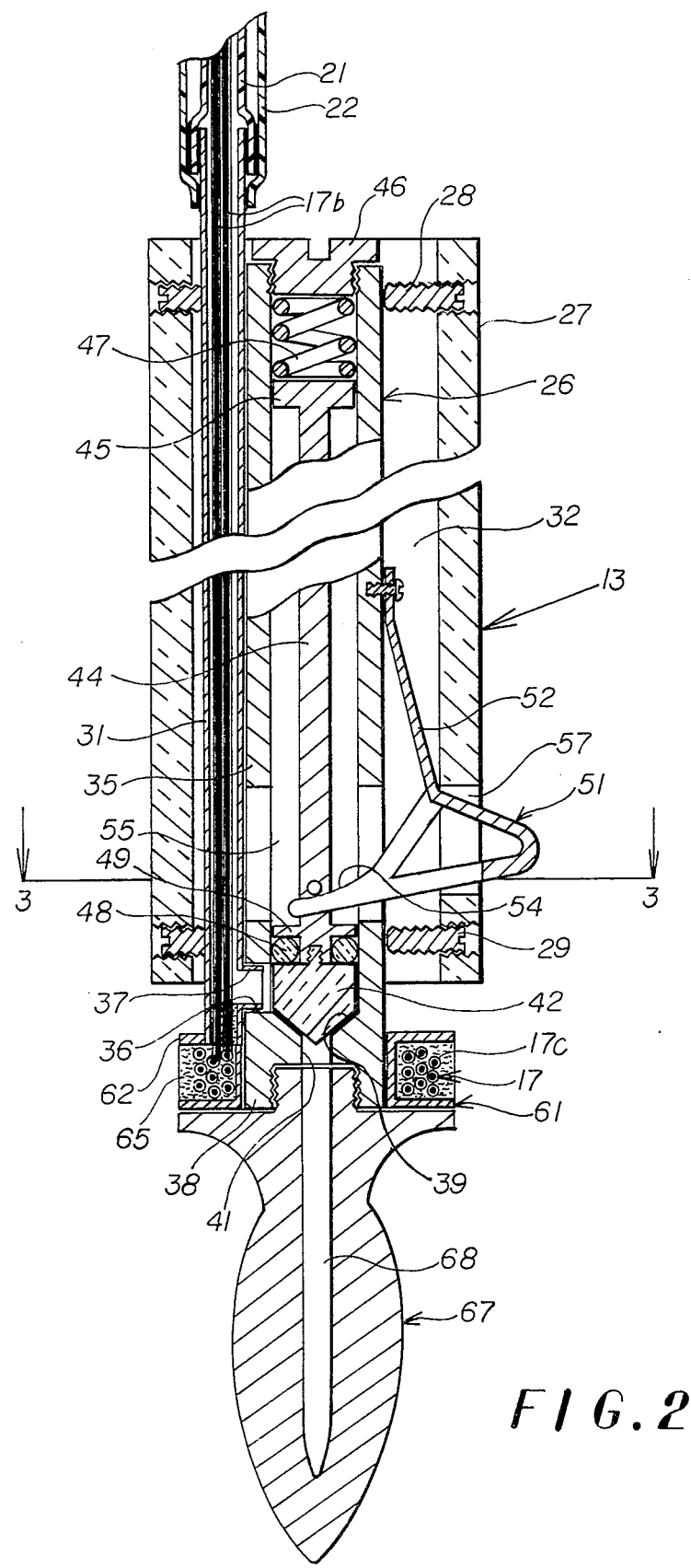
FIG. 2 is a schematic cross-sectional view taken through the applicator shown in FIG. 1.

The flexible tube 14 consists of an inner flexible tube 21 and an outer flexible tube 22. As shown in FIG. 1, one end of the inner tube 21 is connected over a nozzle 23 on the lower portion of the container 15 so as to be in fluid communication therewith. A section 17b of the heater wire 17 extends through the outlet nozzle 23 and completely through the inner tube 21 as shown in FIGS. 1 and 2. Thermal isolation for the inner tube 21 is provided by an annular volume between the inner tube 21 and the outer tube 22.

Figure 3:
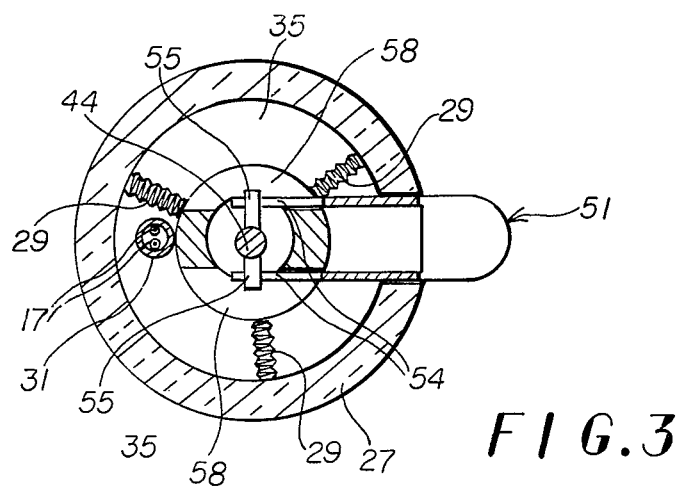
FIG. 3 is a schematic cross-sectional view taken along the lines 3—3 of FIG. 2.

Referring now to FIGS. 2 and 3, the applicator 13 includes a hollow cylindrical body unit 26 enclosed by a hollow cylindrical handle 27. Coaxial alignment between the body unit 26 and the handle 27 is provided by a plurality of upper set screws 28 and a plurality of lower set screws 29. The set screws 28 and 29 extend through threaded openings in the handle 27 and engage the outer surface of the body unit 26. Also included in the applicator 13 is a supply tube 31 having an upper end connected with the inner flexible tube 21 so as to be in fluid communication therewith. The supply tube 31 extends longitudinally within an annular cavity 32 formed between the body unit 26 and the handle 27.

The body unit 26 includes a shell 35 that defines adjacent to its lower end a transverse inlet feed opening 36. Received by the feed opening 36 is a fitted snout 37 extending transversely from the lower end of the supply tube 31. A valve body 38 is formed on the lower end of the shell 35 and defines a tapered valve seat 39 and a valve opening 41. Disposed within the shell 35 is a valve member 42 that can be axially moved relative to the seat 39 so as to control fluid flow through the valve opening 41. A valve stem 44 is axially disposed within the shell 35 and extends between the valve member 42 and an upper shoulder 45. Positioned above the upper shoulder 35 is a spring member 47 that engages a threaded plug 46 in an upper opening of the shell 35. The spring closure of the valve 42 stops wax flow after a desired volume of molten wax has accumulated within the spatula 67. The heating current flow through the conductive wire section 17b generates heat that maintains the molten state of the wax within the inner tube 21 and the supply tube 31. Similarly, the molten state of wax within the spatula 67 is maintained by heat generated in the heater wire section 17c. Heat transfer between the heater wire section 17c and both the valve body 38 and the spatula 67 are insured by a good heat transfer path therebetween. A user of the device 11 can then hand manipulate the applicator 13 to create a wax model with the molten wax available in the spatula 67.

Figure 4:
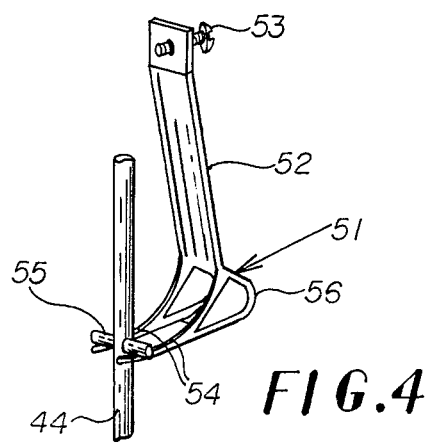
FIG. 4 is a schematic perspective view illustrating a valve operator mechanism shown in FIGS. 2 and 3.
Figure 5:
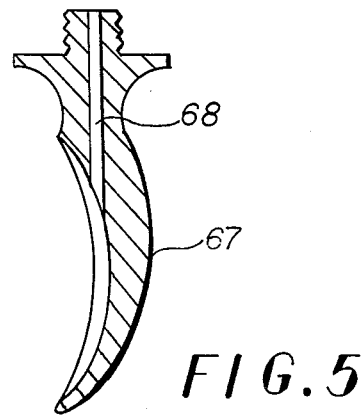
FIG. 5 is a schematic cross-sectional view taken along the lines 5—5 of FIG. 1.

During use of the applicator 13, the rate of wax flow is easily controlled by actuation of the operator unit 51 shown in FIGS. 2-4. Furthermore, the operator 51 can be easily actuated by a finger of a hand manipulating the applicator 13 thereby freeing a user's other hand for other required activities. The application of pressure on the operator portion 56 forces the body portion 52 inwardly and causes the bifurcated camming portions 54 to exert an upward force on the pins 55. In response to that force, the valve stem 44 is forced upwardly against the bias of the spring member 47 withdrawing the valve 42 from the valve seat 39. The degree of this valve opening movement is variably dependent on the degree to which the operator 51 is forced inwardly. Thus, the valve 42 can be easily adjusted in positions between full open and full closed to establish a desired wax flow rate.

Figure 6:
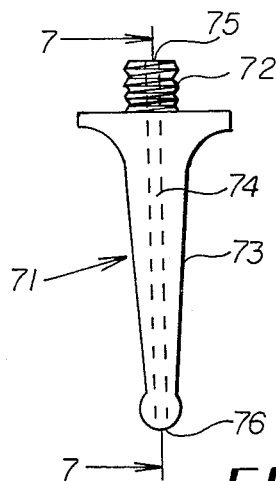
FIG. 6 is a schematic elevational view of a modified dispenser head for use with the applicator unit shown in FIG. 2.
Figure 7:
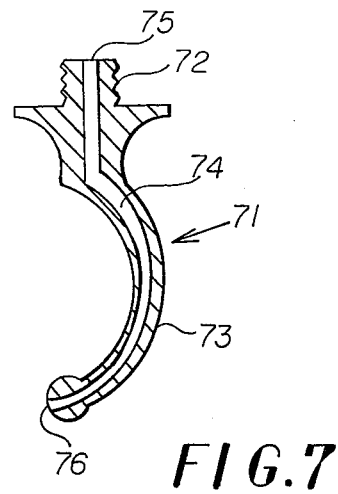
FIG. 7 is a schematic cross-sectional view taken along the lines 7—7 of FIG. 6.

In certain situations, the application of wax to the underside of a model is desirable. Such a procedure is not easily accomplished with the open spatula 67 since an inverted positioning thereof will result in spillage of the retained wax. For those applications, there is provided a modified dispenser head 71 shown in FIGS. 6 and 7. The head 71 has a threaded hub portion 72 that can be threaded into the valve body 38 (FIG. 2) after removal of the spatula head 67. As shown, the head 71 comprises an elongated body portion 73 that defines a coextensive feed channel 74. After engagement of the head 71 with the applicator 13, an entrance 75 to the feed channel 74 is aligned with the valve opening 41. Thus, wax egressing from the valve opening 41 flows through the feed channel 74 and exits through an outlet 76 defined by the outer end of the head 71. Molten wax discharge from the outlet 76 can be directly applied to the underside of a work piece with the applicator 13 in an inverted position.

Obviously, many modifications and variations of the present invention are possible in light of the above teachings. For example only, dispenser heads having configurations other than those specifically shown can be employed with the disclosed device. It is to be understood, therefore, that the invention can be practiced otherwise than as specifically described.

What is claimed is:

1. A molten substance dispenser comprising: container means for a liquified substance to be dispensed; applicator means for receiving the liquified substance from said container means and for applying the substance to a work piece, said applicator means adapted for hand manipulation and defining a discharge port for dispensing the liquified substance flowing from said container means;

flexible tube means connected between said container means and said applicator means and adapted to accomodate the flow of the liquified substance therebetween;

heater means for heating the liquified substance in each of said container means, said applicator means, and said flexible tube means; said heater means comprising electrically conductive wire means extending through said flexible tube, and power supply means for producing heating current flow through said wire means; and valve means for controlling the flow of the liquified substance and supported by said applicator means; said valve means comprising a valve member for controlling the flow through said discharge port, bias means biasing said valve member in a closed position, and an operator for opening said valve member and adapted for operation by a finger on a hand manipulating said applicator means; said operator being a manually actuated cam member which forcibly engages said valve member to produce movement thereof toward an open position.

2. The dispence of claim 1 wherein said applicator includes a spatula for shaping material deposited by said dispenser.

3. A dispenser according to claim 1 wherein said wire means comprises a section disposed in heat exchanging relationship with said container means.

4. A dispenser according to claim 3 wherein said wire means further comprises another section disposed in heat exchanging relationship with said applicator means.

5. A dispenser according to claim 1 wherein said applicator means comprises a plurality of interchangeable dispenser heads for applying the liquified substance to a work piece.

6. A dispenser according to claim 5 wherein said wire means comprises a section disposed in heat exchanging relationship with said container means.

7. A dispenser according to claim 4 wherein said wire means further comprises another section disposed in heat exchanging relationship with said dispenser head.

* * * * *